(12) United States Patent
Yoon et al.

(10) Patent No.: US 10,751,274 B1
(45) Date of Patent: Aug. 25, 2020

(54) FAST-ACTING MICELLE NANOPARTICLE AND COSMETIC COMPOSITION COMPRISING SAME

(71) Applicant: FOREST COMPANY, Seoul (KR)

(72) Inventors: Jong Seong Yoon, Seoul (KR); Dong Myong Kim, Seoul (KR); In Suk Han, Seoul (KR)

(73) Assignee: FOREST COMPANY, Seoul (KR)

( * ) Notice: Subject to any disclaimer, the term of this patent is extended or adjusted under 35 U.S.C. 154(b) by 0 days.

(21) Appl. No.: 16/753,624

(22) PCT Filed: Oct. 1, 2018

(86) PCT No.: PCT/KR2018/011631
§ 371 (c)(1),
(2) Date: Apr. 3, 2020

(87) PCT Pub. No.: WO2019/088458
PCT Pub. Date: May 9, 2019

(30) Foreign Application Priority Data

Oct. 31, 2017 (KR) ........................ 10-2017-0143761

(51) Int. Cl.
| *A61K 8/68* | (2006.01) |
| *A61K 8/02* | (2006.01) |
| *A61K 8/63* | (2006.01) |
| *A61Q 19/00* | (2006.01) |

(52) U.S. Cl.
CPC .............. *A61K 8/68* (2013.01); *A61K 8/0291* (2013.01); *A61K 8/63* (2013.01); *A61Q 19/00* (2013.01)

(58) Field of Classification Search
None
See application file for complete search history.

(56) References Cited

FOREIGN PATENT DOCUMENTS

| JP | 2002535349 A | 10/2002 |
| KR | 101514970 B1 | 4/2015 |
| KR | 1020150076533 A | 7/2015 |
| KR | 1020150103503 A | 9/2015 |
| KR | 101577874 B1 | 12/2015 |
| KR | 1020170119642 A | 10/2017 |

OTHER PUBLICATIONS

International Search Report for International application No. PCT/KR2018/011631, dated Mar. 22, 2019, 4 pages, ISA/KR.
Lee, Jeong Pyo et al., Preparation of Phytosphingosine-I-phosphate Nano-liposome and Its in Vivo Anti-aging Improvement Effects of Finished Products, Korean Journal of Aesthetics and Cosmetology, 2012, pp. 941-948, vol. 10 No. 4.

*Primary Examiner* — Brian J Davis
(74) *Attorney, Agent, or Firm* — Lucas & Mercanti, LLP (57) ABSTRACT

The present invention relates to phytosphingosine-1-phosphate micelle nanoparticles having high transdermal penetration and absorption rates. In addition, the present invention relates to a cosmetic composition containing the micelle nanoparticles and a skin care method using the same.

3 Claims, 9 Drawing Sheets

FAST-ACTING MICELLE NANOPARTICLE AND COSMETIC COMPOSITION COMPRISING SAME

CROSS-REFERENCE TO RELATED APPLICATIONS

This application is a 371 U.S. national stage of PCT/KR2018/011631, filed Oct. 1, 2018, which claims the priority from Korean Patent Application No. 10-2017-0143761, filed Oct. 31, 2017, the contents of each of which are incorporated herein by reference.

TECHNICAL FIELD

The present invention relates to fast-acting micelle nanoparticles and a cosmetic composition containing the same.

BACKGROUND ART

Phytosphingosine phosphate (PhS-1-P, P1P) is an analog of sphingosine-1-phosphate (S1P) secreted from platelets and exhibits the same efficacy as sphingosine-1-phosphate. When a human body is hurt or exposed to extreme stress, in order to overcome the hurt or stress, the human body secretes various growth factors and stress relief materials through platelets of the blood. Among the cell regeneration induction materials thus secreted, there is a material called sphingosine-1-phosphate (S1P). This material promotes angiogenesis and cell migration, which contributes to wound healing and preventing the death of cells exposed to stress and activating cells. Moreover, it promotes collagen production through the proliferation of dermal cells and protects cells from death by exposure to ultraviolet rays. In addition, reports on prevention of infertility and birth defects by inhibiting gene damage caused by radiation exposure have been published. S1P (sphingosine-1-phosphate), which has such efficacy, is receiving attention as an anti-aging cosmetic and pharmaceutical raw material, but is difficult to commercialize due to the price thereof of 400 million won per gram. Hence, the material developed therefor is P1P (phytosphingosine-1-phosphate). P1P has a similar structure to that of S1P (sphingosine-1-phosphate) and is known to exhibit the same efficacy.

Sphingosine-1-phosphate acts on receptors on the cell surface to thus cause various responses. Five types of receptors of S1P are known (S1P1, S1P2, S1P3, S1P4, and S1P5). Phytosphingosine-1-phosphate (P1P), a structural analog of S1P, binds to the same receptor as S1P and performs the same function in cells. P1P is a special agonist that binds to S1P1 and S1P4 better than S1P. Therefore, P1P also exhibits the effects of cell migration, cell proliferation (inhibition of cell death), angiogenesis, wound healing, and the like. (Korean Patent No. 10-1514970, Korean Patent No. 10-1577874, etc.)

However, the above are solid materials that are not easily dissolved in water or oils, unlike general cosmetic raw materials, and it is difficult to deliver the effect thereof to the skin. The present inventors have studied formulations having the high transdermal absorption rate of phytosphingosine-1-phosphate and have ascertained that it is possible to manufacture fast-acting micelle nanoparticles having superior transdermal absorption rate and skin improvement ability when using bile acid, thus culminating in the present invention.

DISCLOSURE

Technical Problem

An objective of the present invention is to provide phytosphingosine-1-fast-acting micelle nanoparticles having an increased transdermal absorption rate.

Another objective of the present invention is to provide a cosmetic composition using the fast-acting micelle nanoparticles of the present invention.

Technical Solution

In order to accomplish the above objectives, the present invention provides micelle nanoparticles including bile acid and phytosphingosine-1-phosphate.

In addition, the present invention provides a cosmetic composition containing the micelle nanoparticles.

In addition, the present invention provides a skin care method including treating the skin of a subject with the cosmetic composition containing the micelle nanoparticles.

Advantageous Effects

According to the present invention, micelle nanoparticles including bile acid and phytosphingosine-1-phosphate have high transdermal penetration efficiency and have the ability to increase skin elasticity, skin thickness and skin density.

BEST MODE

Specific structural or functional descriptions presented in the embodiments of the present invention are only illustrated for the purpose of describing the embodiments according to the concept of the present invention, and embodiments according to the concept of the present invention may be implemented in various forms. In addition, the present invention should not be construed as limited to the embodiments described herein, but should be understood to include all modifications, equivalents, and substitutes included in the spirit and scope of the present invention. Hereinafter, a detailed description will be given of the present invention with reference to the accompanying drawings.

The present invention pertains to micelle nanoparticles including bile acid and phytosphingosine-1-phosphate.

In addition, the present invention pertains to a cosmetic composition containing the micelle nanoparticles of the present invention.

In addition, the present invention pertains to a skin care method including treating the skin of a subject with the cosmetic composition containing the micelle nanoparticles of the present invention.

The present invention is specified below.

Bile Acid

The bile acid of the present invention may be typical bile acid, and the kinds thereof are not particularly limited. Examples of bile acid of the present invention may include cholic acid, chenodeoxycholic acid, glycocholic acid, taurocholic acid, deoxycholic acid, lithocholic acid, and the like. Preferably, the bile acid is taurocholic acid but is not limited thereto. The bile acid of the present invention may be separated from natural products such as porcine bile, etc., or may be chemically synthesized.

Phytosphingosine-1-Phosphate

The phytosphingosine-1-phosphate of the present invention may be typical phytosphingosine-1-phosphate, but is not particularly limited.

Micelle Nanoparticles of the Present Invention

The present invention pertains to fast-acting micelle nanoparticles. Preferably, the present invention pertains to fast-acting micelle nanoparticles including bile acid and phytosphingosine-1-phosphate. The bile acid and phytosphingosine-1-phosphate are conjugated to each other. The micelle nanoparticles have a size of 100 to 200 nm, preferably 110 to 190 nm, and more preferably 120 to 180 nm. Within the above size range, the micelle nanoparticles of the present invention facilitate transdermal penetration and absorption, effectively improving the state of the skin.

The micelle nanoparticles of the present invention include lysolecithin as a surfactant. The micelle nanoparticles of the present invention, including lysolecithin, have high transdermal penetration and transdermal absorption rates.

Figure 1:
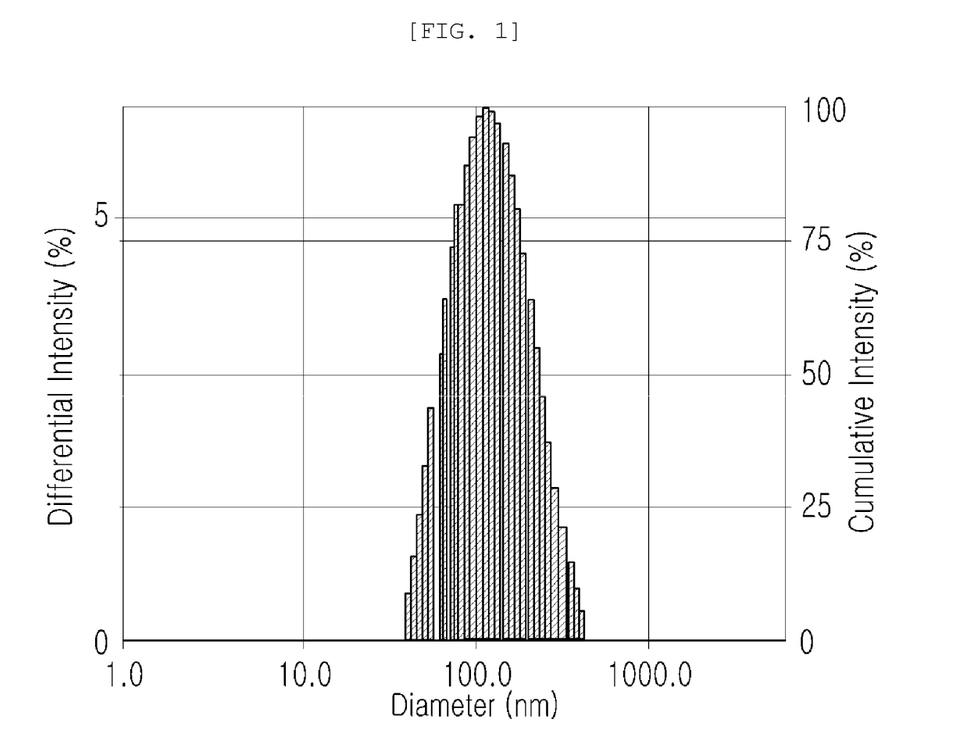
FIG. 1 shows the particle distribution of PhS1P-bile acid-conjugated micelle nanoparticles.
Figure 2:
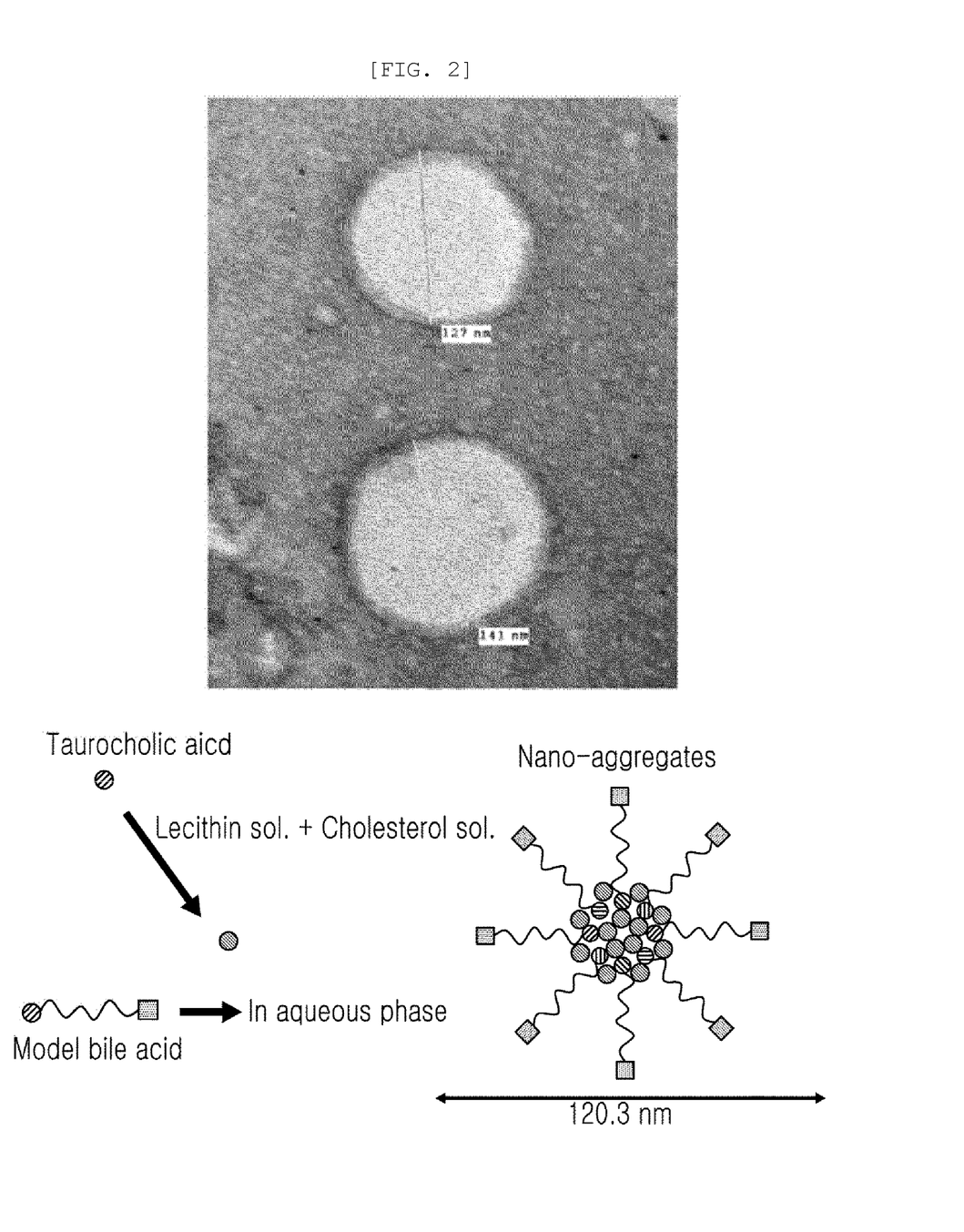
FIG. 2 is an image showing the PhS1P-bile acid-conjugated micelle nanoparticles.

As shown in FIGS. 1 and 2, based on the results of measurement, using a Photal ELS-Z, of the particle distribution of the manufactured micelles containing 0.1% PhS1P, the micelle nanoparticles of the present invention are spherical, with an average particle size of 120 to 150 nm. Considering that the distance between intercellular lipids is 100 to 200 nm, the micelle nanoparticles of the present invention are found to be micelles having superior transdermal penetration and absorption performance.

Cosmetic Composition

The cosmetic composition of the present invention has the ability to increase skin elasticity, skin thickness and skin density.

The cosmetic composition of the present invention may be manufactured in any formulation that is commonly prepared in the art, and may be formulated into a solution, suspension, emulsion, paste, gel, cream, lotion, powder, soap, surfactant-containing cleanser, oil, powder foundation, emulsion foundation, wax foundation and spray, etc., but is not limited thereto. Moreover, the cosmetic composition of the present invention may be manufactured in the form of a softening skin lotion, nourishing skin lotion, nourishing cream, massage cream, essence, eye cream, cleansing cream, cleansing foam, cleansing water, pack, spray or powder formulation.

Skin Care Method

The present invention pertains to a skin care method including treating the skin of a subject with the cosmetic composition containing the micelle nanoparticles of the present invention. The skin care includes increasing skin elasticity, increasing skin thickness, and increasing skin density.

The advantages and features of the present invention and methods of achieving the same will be apparent with reference to the embodiments described below in detail. However, the present invention is not limited to the examples disclosed herein, and may be embodied in different forms. These embodiments are provided to complete the disclosure of the present invention and to sufficiently transfer the scope of the present invention to those skilled in the art, and the present invention is merely defined by the scope of the claims.

<Material and Method>

Measurement of Skin Elasticity

Skin elasticity was measured using a cutometer MPA580 (Courage and Khazaka, Germany) for measuring elasticity. The elasticity was measured based on the principle whereby the skin is sucked into the probe for the measurement time by continuous negative pressure and then the skin returns to its original appearance when the negative pressure is removed. The measurement method was performed in a non-invasive manner after close contact of the probe, having a diameter of 2 mm and connected to the instrument, with the skin. In this test, the measurement condition was mode 1.

Mode 1 condition is negative pressure of 450 mbar kept constant, suction time of 2 sec, and relaxation time of 2 sec, and measurement was performed three times in succession to determine the arithmetic mean, thus obtaining measurement results. The unit of measure is A.U. (arbitrary units). In this test, the variable R2 (net elasticity), which is considered to be directly related to elasticity characteristics, was used. The improvement rate of skin elasticity was calculated using the following Equation 1.

$$\text{Improvement rate (\%)} = (\text{measured value after use of sample} - \text{measured value before use of sample} / \text{measured value before use of sample}) \times 100 \quad \text{<Equation 1>}$$

Measurement of Skin Thickness and Dermal Density

The skin thickness and the dermal density were measured in a manner in which a gel for ultrasound testing was applied on Dermascan-C(Cortex Technology, Denmark), which is a device for high-resolution 20 MHz ultrasound imaging, and the probe was positioned at a right angle to the skin and then pressed slightly on the side of the cheek. The range of analysis was limited from just below the epidermis to the upper part of the subcutaneous fat layer, and the intensity, which is a parameter representing the dermal density, was measured and analyzed, and the skin thickness was also measured and analyzed. High measured values resulted when the skin thickness and the dermal density were high, and low measured values resulted when the skin thickness and the dermal density were low. The improvement rates of skin thickness and dermal density were calculated using the following Equation 1.

$$\text{Improvement rate (\%)} = (\text{measured value after use of sample} - \text{measured value before use of sample} / \text{measured value before use of sample}) \times 100 \quad \text{<Equation 1>}$$

Evaluation of Safety of Subject

Whether adverse effects on the subjects' skin occurred was closely observed, and the grade thereof was represented depending on the severity of the adverse effects when they appeared. The evaluation of adverse effects was determined based on the presence or absence of erythema, edema, scaling, itching, pain, burning, stiffness, tingling and the like. If there was a difference between the evaluations of two dermatologists, the higher evaluated value was taken.

Statistical Analysis Method

Significance before/after sample application was confirmed by a hypothetical mean difference of 5% ($p<0.05$) through a paired t-test performed on values measured using an instrument, and Microsoft Excel version 2007 software was used as a statistical analysis program.

<Experimental Example 1> Manufacture of Micelle Nanoparticles

PhS1P was manufactured into a formulation applicable on the skin by optimizing efficient skin penetration absorption, particle size, particle surface charge, magnitude of zeta potential, and pH, and was dissolved in a 10 mM HEPES ((4-(2-hydroxyethyl)-1-piperazineethanesulfonic acid)) buffer solution having a pH of 6.0 to 7.5, and the average particle size, particle surface charge, and absolute value of zeta potential thereof were measured.

Therefore, the micelle nanoparticles of the present invention had an average particle size of 120.3 nm, a surface change of −5 mV to +5 mV, and an absolute value of zeta potential of 3 mV to 18 mV.

Example 1

5.78 g of taurocholic acid was mixed with 25 ml of methanol (methanol:water at a volume ratio of 85:15) to afford a 430 mM taurocholic acid solution. 2.25 ml of the taurocholic acid solution was added with 1.8 ml of a lecithin solution (obtained by dissolving lecithin at 100 mg/ml in chloroform) and 1.05 ml of a cholesterol solution (obtained by dissolving cholesterol purified by a methanol method at 500 mg/ml in a chloroform solvent), thus preparing a primary solution.

The primary solution thus obtained was placed in a glass tube with a Teflon cap, and was heat-treated in a water bath at 55° C. for 5 hr. The primary solution was then evaporated using nitrogen gas until it was sticky, thick and yellowish. The evaporation residue was frozen at −70° C. for 2 hr, and the tube was opened, followed by lyophilization under reduced pressure for 9 hr or more, dissolution again in PBS, and heat treatment at 56° C. for 4 hr. After completion of heat treatment, the resulting solution was diluted at 1:10 (by volume) in a serum-free medium and filtered using a 0.45 µm filter, thereby manufacturing PhS1P-bile acid-conjugated micelle nanoparticles.

Example 2

Micelle nanoparticles were manufactured in the same manner as in Example 1, with the exception that lecithin was used alone. In Example 2, lysolecithin was not used when manufacturing the micelle nanoparticles.

Experimental Example 2

The particle size distribution (ELS-Z, Photal, Japan) of the PhS1P-bile acid-conjugated micelle nanoparticles manufactured in Example 1 was measured, and the particle shape thereof was observed using an SEM (JEM1010, JEOL, Japan). The presence or absence of PhS1P in the manufactured PhS1P-bile acid-conjugated micelle nanoparticles was confirmed using HPLC (Agilent 1200, Germany).

Based on the results of measurement, using a Photal ELS-Z, of the particle distribution of the manufactured PhS1P-bile acid-conjugated micelle nanoparticles containing 0.1% PhS1P, the particle size thereof was determined to be 158.4 nm (FIG. 1). The distance between intercellular lipids was 100 nm to 200 nm, and the particle size of the PhS1P-bile acid-conjugated micelle nanoparticles containing 0.1% PhS1P was 158.4 nm, indicating that the transdermal absorption of the manufactured PhS1P-bile acid-conjugated micelle nanoparticles was good.

Meanwhile, since the particle size of the manufactured PhS1P-bile acid-conjugated micelle nanoparticles was too small to be measured using a general optical microscope, an image taken using a cryo-electron microscope was analyzed (FIG. 2). The convex portion in the image is PhS1P-bile acid-conjugated micelle nanoparticles, indicating that the PhS1P-bile acid-conjugated micelle nanoparticles were formed well.

Also, the stability of the PhS1P-bile acid-conjugated micelle nanoparticles was tested at 45° C. and −4° C. according to a general cosmetic formulation stability test method, from which it was visually confirmed that the formulation of PhS1P-bile acid-conjugated micelle nanoparticles remained stable for 2 months.

<Experimental Example 3> Evaluation of Inclusion of PhS1P in Micelle Nanoparticles In order to evaluate whether PhS1P was present in the PhS1P-bile acid-conjugated micelle nanoparticles manufactured in Example 1, HPLC was performed. An Agilent 1200 model HPLC (Agilent 1200, Germany) was used therefor, conditions of absorbance at 214 nm and columns of ZORBAX Eclipse XDB-C18, 5 µm size, and 4.6 mm×150 mm were applied, and a mobile phase composed of methanol and purified water at 50 vol %:50 vol % was used. The flow rate was 0.8 ml/min, and the elution time at 30° C. was 10 to 16 min. A reference material was composed of methanol and purified water at 95 vol %:5 vol %, and the samples were also subjected to the same conditions and sonicated for 1 hr before use.

Therefore, the same peak appeared in the reference material and the PhS1P-bile acid-conjugated micelle nanoparticles. Accordingly, it was confirmed that PhS1P was present in the manufactured PhS1P-bile acid-conjugated micelle nanoparticles in Experimental Example 1, and also that PhS1P was able to be stably formulated using the PhS1P-bile acid-conjugated micelle nanoparticles (FIG. 3 (A): reference material, (B): PhS1P micelle nanoparticles).

<Experimental Example 4> Evaluation of Transdermal Absorption

The micelle nanoparticles manufactured in Example 1 and Example 2 were evaluated for transdermal absorption. Specifically, female hairless guinea pigs (strain IAF/HA-hrBR) about 8 weeks old were used. The abdominal skin of the guinea pigs was excised, mounted to a Franz-type diffusion cell (Lab fine instruments, Korea) and evaluated. A 50 mM phosphate buffer (pH 7.4, 0.1 M NaCl) was placed in the receptor compartment (5 ml) of the Franz-type diffusion cell, after which the diffusion cell was mixed and dispersed at 32°

C. and 600 rpm, and 50 μl of the PhS1P-bile acid-conjugated micelle nanoparticles were placed in a donor compartment. Absorption and diffusion were conducted over a preset time (12 hr, 24 hr), and the portion in which absorption and diffusion occurred was 0.64 cm deep from the skin. After completion of absorption and diffusion of the active ingredient, the emulsion that was not absorbed but remained on the skin was washed with dried Kimwipes or 10 ml of ethanol, the skin into which the active ingredient was absorbed and diffused was homogenized using a tip-type homogenizer, and the micelle nanoparticles absorbed into the skin were extracted with 4 ml of dichloromethane. Thereafter, the extract was filtered with a 0.45 μm nylon membrane, and the amount thereof was measured through HPLC under the following conditions.

The micelle nanoparticles manufactured using typical lecithin in Example 2 exhibited a transdermal absorption amount of 0.3577, and the PhS1P-bile acid-conjugated micelle nanoparticles of Example 1 exhibited a transdermal absorption amount of 0.5101. Therefore, it was confirmed that the transdermal absorption rate was increased by about 43% in the manufactured PhS1P-bile acid-conjugated micelle nanoparticles (Table 1).

TABLE 1

| Nanoparticles | Transdermal absorption amount (μg) |
|---|---|
| PhS1P-bile acid-conjugated nanoparticles (Example 1) | 0.5101 |
| Typical lecithin nanoparticles (Example 2) | 0.3577 |

Based on the results of evaluation of stability of the micelle nanoparticles of Example 1 for 2 months, it was confirmed that there was no abnormality in stability over time. These nanoparticles had an average particle size of 120.3 nm based on the particle distribution and are thus expected to easily pass through intercellular lipids. Based on the results of testing of transdermal penetration absorption amounts, good transdermal absorption was confirmed. The PhS1P-bile acid-conjugated micelle nanoparticles were an active material having a large molecular weight by the combination of skin-like PhS1P, lecithin and sugar ester, but exhibited high bioavailability even when used in a small amount.

<Experimental Example 5> Evaluation of Transdermal Penetration

In order to evaluate the transdermal penetration rate of the micelle nanoparticles of Example 1, a mouse skin penetration experiment was performed through a Franz diffusion cell using the micelle nanoparticles as a sample. The mouse skin was extracted from the back of ICR outbred albino mice (12-week-old, about 50 g, females), which were killed by cervical dislocation. The subcutaneous fat was removed from the extracted skin (1.5 cm×1.5 cm) so that the skin was not hurt, and the dermis was used without being removed. The skin was fixed between the donor and the receptor phase so that the stratum corneum part of the back skin of the prepared ICR mice faced upwards.

The transepidermal area contacting the receptor phase was 0.6362 cm$^2$, and the receptor phase was a mixed solution of 2.0% HCO-60 (in 20% ethanol), showing the highest solubility in the preliminary experiments. 5 ml of the receptor phase was placed in a Franz diffusion cell, and the temperature was maintained at 37.0±0.5° C. using a constant-temperature water bath. Stirring to homogeneity was performed at 150 rpm for 24 hr. 0.5 ml of each sample was applied to the transepidermal surface of the donor, after which 0.75 ml of the receptor phase was collected every 8 hr (a total of 3 times) for 24 hr through a sampling port using a 1 ml syringe and stored in a 1.5 ml tube. Immediately after collection, supplementation with the same amount of the receptor solution was conducted. As such, the collected sample was analyzed through HPLC in order to quantify quercetin and rutin therein.

In order to measure the amount of PhS1P remaining on the skin, unpenetrated samples were washed three times with PBS immediately after taking the skin out of the diffusion cell. After washing, tape stripping was performed 3 times on the skin portion that contacted the sample, after which the tape-stripped skin was sliced, the tape and the skin were placed in respective 10 ml falcon tubes, 7 ml of ethanol was added thereto, and PhS1P remaining on the tape and skin was extracted using a sonicator (ultrasound generator) for 90 min. The ethanol was evaporated to dryness, after which PhS1P was dissolved again in 0.75 ml of ethanol, and the amount of PhS1P remaining on the skin was quantified through HPLC.

In order to evaluate the skin absorption capacity of the 2.0% PhS1P-bile acid-conjugated micelle nanoparticles of Example 1 containing 0.1% PhS1P, a penetration experiment was performed using a Franz diffusion cell. Here, a PhS1P solution was used as a control.

Figure 4:
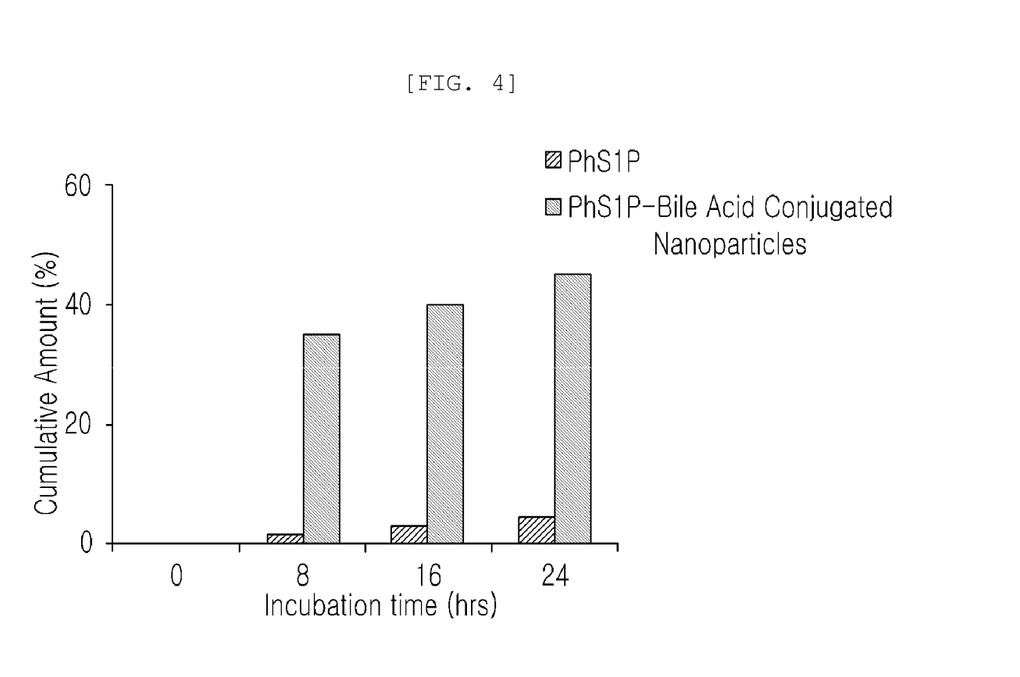
FIG. 4 shows the in-vitro skin penetration rate profile of the PhS1P-bile acid-conjugated micelle nanoparticles of Example 1 and a control (PhS1P) that penetrated the ICR mouse skin.

Based on the experimental results using the Franz diffusion cell (5 ml) after 24 hr by measuring the final cumulative penetration rate and amount of the sample collected every 8 hr, the amount of PhS1P that penetrated the skin was 2.52 μg in the control (PhS1P solution), and was 46.93 μg in the PhS1P-bile acid-conjugated micelle nanoparticles of Example 1 (FIG. 4).

Figure 5:
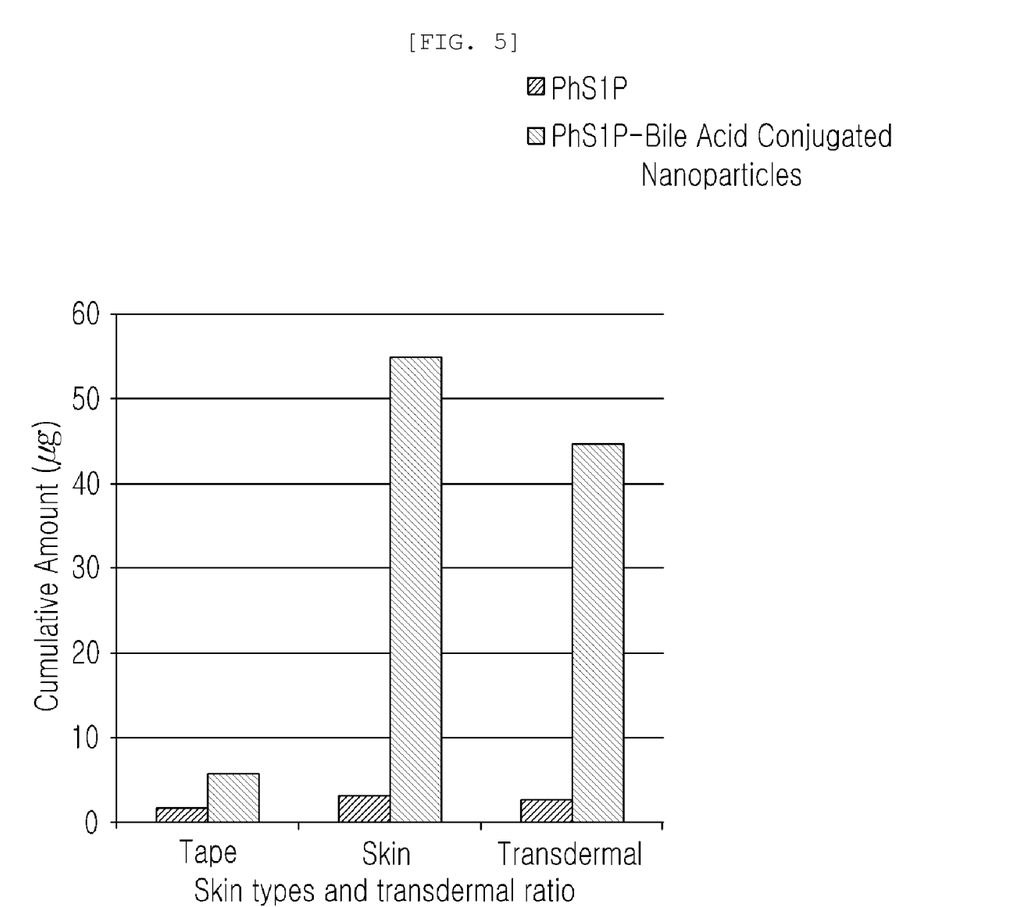
FIG. 5 shows the total profile of in-vitro skin penetration amounts of the PhS1P-bile acid-conjugated micelle nanoparticles of Example 1 and the control (PhS1P) that penetrated the ICR mouse skin.

Also, based on the results of measurement of the total penetration amount of PhS1P remaining in the stratum corneum through tape stripping, the amount of PhS1P was 1.81 μg in the control (PhS1P solution) and was 5.90 μg in the PhS1P-bile acid-conjugated micelle nanoparticles of Example 1. On the other hand, in the case of PhS1P remaining on the skin, the amount of PhS1P present in the skin was 2.72 μg in the control and was 48.21 μg in the PhS1P-bile acid-conjugated micelle nanoparticles of Example 1. Therefore, it was confirmed for the PhS1P-bile acid-conjugated micelle nanoparticles of Example 1 that the active material infiltrated the skin in an amount greater than the control (FIG. 5).

Experimental Example 6

In order to manufacture a cosmetic product containing the PhS1P-bile acid-conjugated micelle nanoparticles of Example 1 as an active ingredient, a serum formulation containing 1.5% of PhS1P-bile acid-conjugated micelle nanoparticles was manufactured. In general, a serum formulation is a product widely used by consumers and is expected to alleviate skin aging. The ingredients other than the PhS1P-bile acid-conjugated micelle nanoparticles consisted of components commonly used in serum formulations. In order to evaluate the efficacy of skin anti-aging products, a human application test was conducted to determine improvements in skin elasticity, skin thickness, and dermal density.

The human application test was carried out according to standard work instructions from an external human study professional institution. Subjects were selected according to subject selection and exclusion criteria, and all matters related to the test were verbally conveyed in advance. The subjects, who voluntarily participated in the study, indicated consent to the human application test, and the test was performed.

21 female subjects were finally selected for the clinical trial of the serum product, and the product efficacy for improving skin elasticity, skin thickness, and dermal density was evaluated. Reduced skin elasticity is a skin aging phenomenon that all ages are concerned about. Therefore, subjects in their 30s to 50s (average age: 46.2 years) were tested in order to confirm the improvement effect in all ages. The subjects visited a total of four times (0 weeks before the human application test, after 2 weeks of use, after 4 weeks of use, and after 8 weeks of use) during the human application test. The subjects for the human application test were prohibited from using basic skin care products and makeup for 12 hr before the visit. The human application test was conducted under constant-temperature and constant-humidity conditions (20 to 24° C., 40 to 60% RH) without air movement or direct sunlight. After facial washing, the subjects were stabilized under constant-temperature and constant-humidity conditions for 30 min and then treated.

Figure 6:
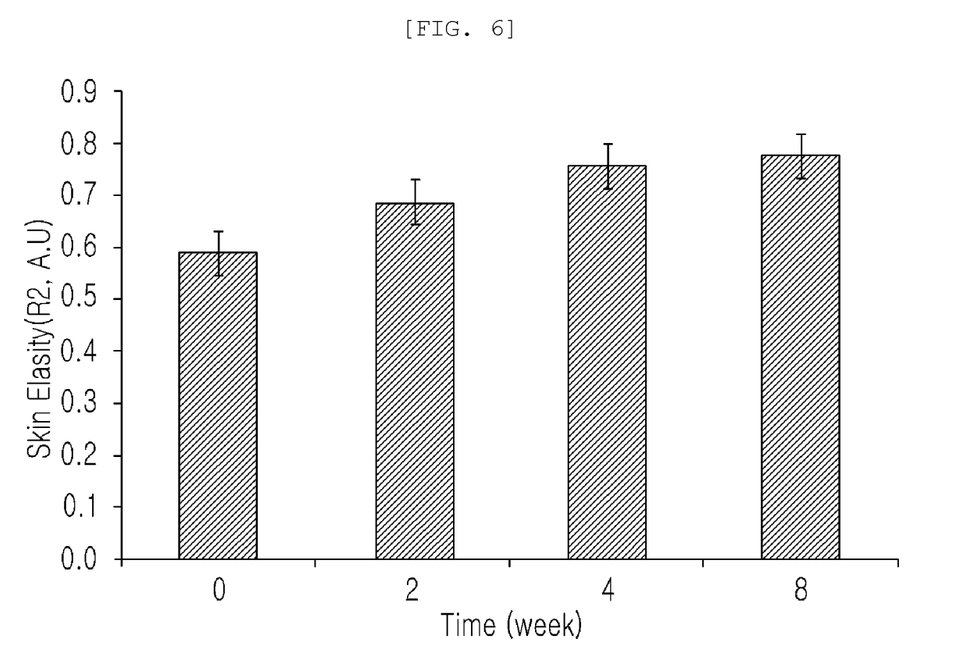
FIG. 6 shows the ability of a cosmetic formulation using the PhS1P-bile acid-conjugated micelle nanoparticles of Example 1 to increase skin elasticity.

When using the product containing the PhS1P-bile acid-conjugated micelle nanoparticles of Example 1, the skin elasticity was increased by 16.21% after 2 weeks of use, 28.85% after 4 weeks of use, and 39.35% after 8 weeks of use (FIG. 6).

Figure 7:
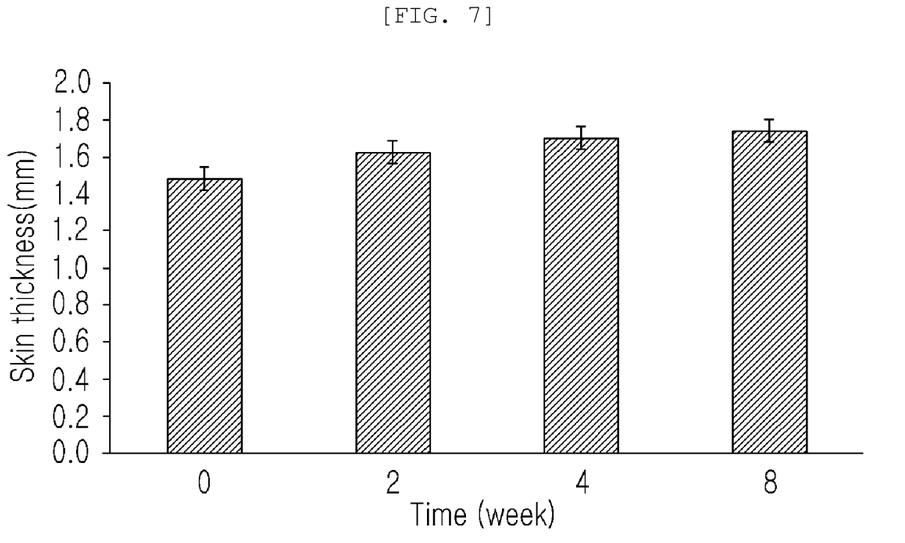
FIG. 7 shows the ability of the cosmetic formulation using the PhS1P-bile acid-conjugated micelle nanoparticles of Example 1 to increase skin thickness.

Also, based on the results of analyzing the skin thickness measurement values using Dermascan-C, when using the product containing the PhS1P-bile acid-conjugated micelle nanoparticles of Example 1, the skin thickness was increased by 10.11% after 2 weeks of sample use, 19.57% after 4 weeks of use, and 27.23% after 8 weeks of use at a statistically significant level (P<0.05) compared to before use (FIG. 7).

Figure 8:
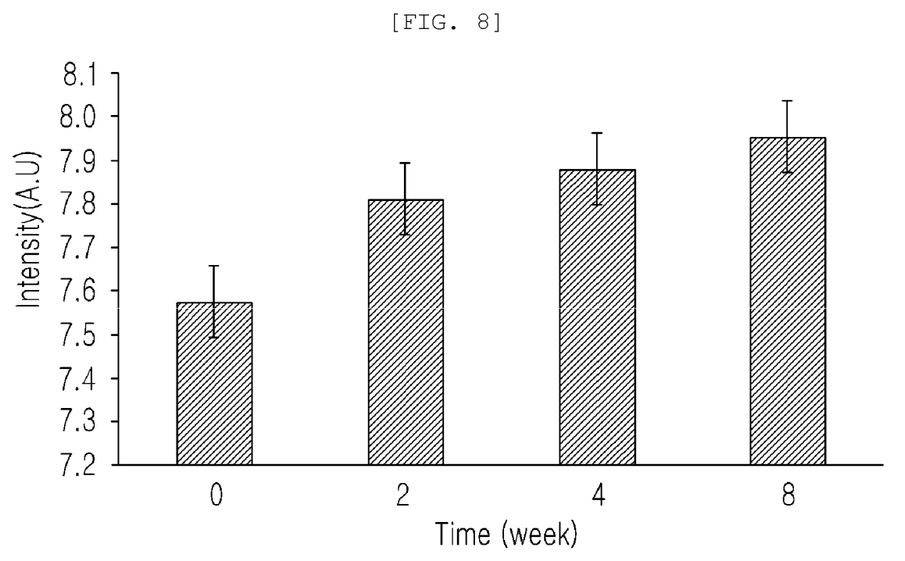
FIG. 8 shows the ability of the cosmetic formulation using the PhS1P-bile acid-conjugated micelle nanoparticles of Example 1 to increase dermal density.
Figure 9:
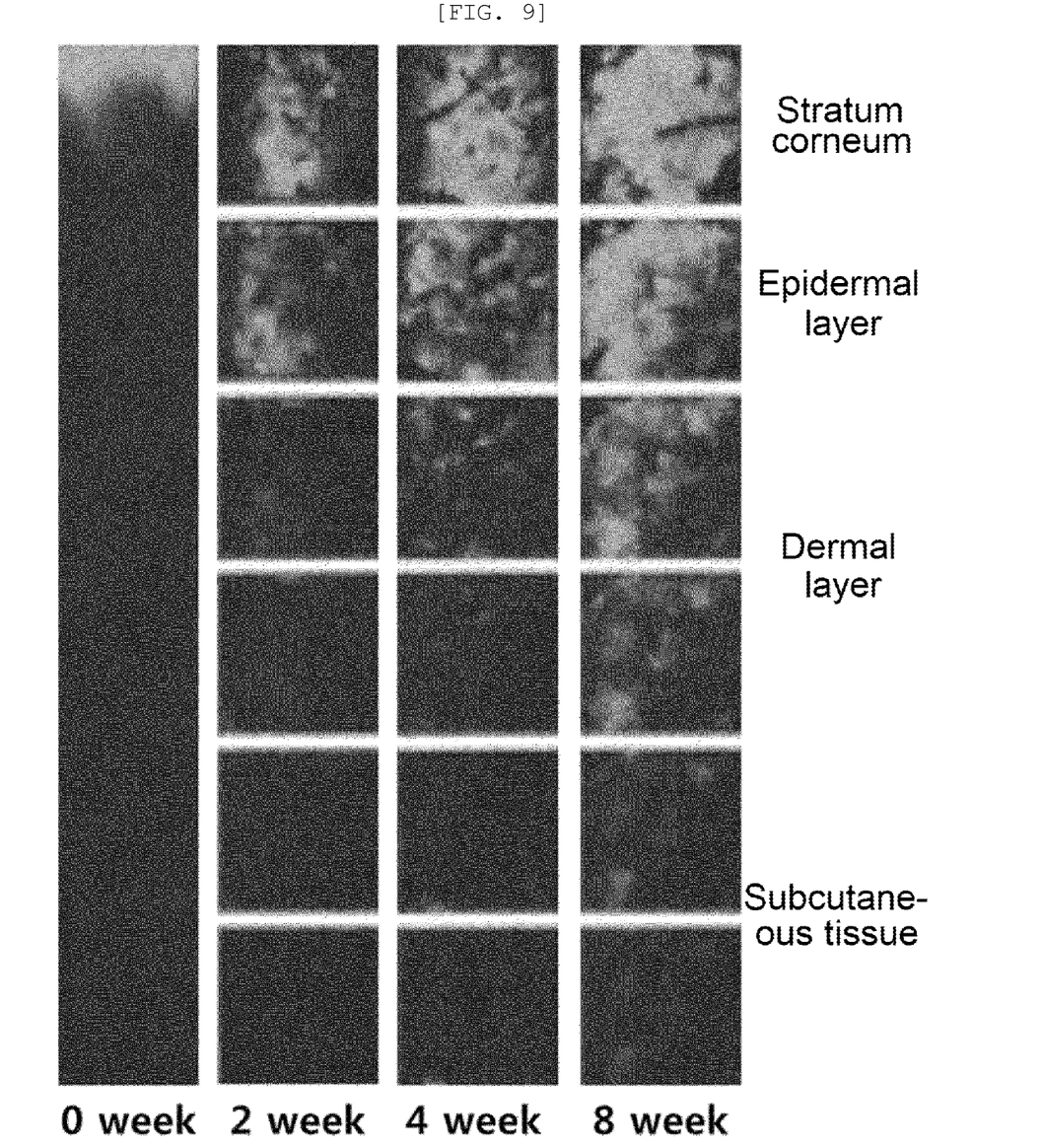
FIG. 9 is images showing the results of measurement of skin density after use of the cosmetic formulation using the PhS1P-bile acid-conjugated micelle nanoparticles of Example 1.

Also, the dermal density was increased by 4.52% after 2 weeks of use, 5.17% after 4 weeks of use, and 7.17% after 8 weeks of use at a statistically significant level (P<0.05) compared to before use of the product containing the PhS1P-bile acid-conjugated micelle nanoparticles of Example 1 (FIG. 8). Moreover, based on the results of observation of skin photographs depending on the period of use of the product, the dermal density was also improved after 4 and 8 weeks of use (FIG. 9).

Based on the results of evaluation of adverse effects on the skin by a dermatologist during the test and the results of a questionnaire evaluation conducted on the subjects, the sample did not show any special adverse effects on the skin (human signs such as blisters and symptoms such as itching complained by patients) during the evaluation period. Therefore, it was confirmed that the cosmetic formulation containing the PhS1P-bile acid-conjugated micelle nanoparticles of Example 1 has an effect of alleviating various skin aging phenomena and thus is an ingredient applicable as a cosmetic material.

Experimental Example 7

The encapsulation efficiency and structure of the micelle nanoparticles of Example 1 were measured. Specifically, the amount of PhS1P was fixed to 0.1%, and 0.5 to 2.0 wt % of the micelle nanoparticles of Example 1 was dissolved in tetrahydrofuran (THF). The resulting solution was allowed to react at 40° C. for 3 hr, added dropwise to 10 ml of deionized water, and stirred for 24 hr, after which the initial solvent was evaporated. In order to measure the encapsulation efficiency of PhS1P, filtration was performed using a 0.45 μm filter, excess ethanol was added to the micelle nanoparticles, which are the polymer passed through the filter, and to PhS1P not passed therethrough, followed by sonication and evaporation of the solvent. 10 ml of ethanol (the same amount as the filtration amount) was added and impurities were removed using a 0.45 μm syringe filter, after which the structure and size of the nanoparticles were measured and the amount thereof was quantified through HPLC. Also, the calibration curve was prepared depending on the concentration of PhS1P, and the encapsulation efficiency of PhS1P in the micelle nanoparticles of Example 1 was then determined using the following Equation 2.

Encapsulation efficiency (%)=(amount of PhS1P in micelle nanoparticles after encapsulation/amount of PhS1P used for encapsulation)×100  <Equation 2>

As shown in FIGS. 1 and 2, micelles containing 0.1% PhS1P were manufactured, and the particle distribution thereof was measured using a Photal ELS-Z. Thus, the micelle nanoparticles of the present invention were spherical, with an average particle size of 120 to 150 nm, which was described in the structure of micelle nanoparticles and the method of manufacturing the micelle nanoparticles in <Experimental Example 1>. More specifically, the particle size and particle size distribution of the micelle nanoparticles were measured using a Photal ELS-Z series (Otsuka Electronics, Japan) for analyzing particle size using light scattering. The measurement temperature was 25° C., the scattering angle was 165°, the light source was an Ar laser, and three particle size measurement trials were performed, with 60 measurements for each trial. The average particle size was represented through cumulative analysis, and the particle size distribution was analyzed using a Contin method. Here, the zeta potential was measured at 25° C., the scattering angle was 165°, the light source was an Ar laser, and the zeta potential of the particles was measured in three trials of 3 measurements each. The zeta potential was analyzed and represented by a Smoluchowski method.

Based on the results of measurement of zeta potential depending on changes in the concentration of the particles as shown in Table 2, typical lecithin nanoparticles containing no PhS1P showed −0.85±0.72 mV at 1.5% concentration, and the micelle nanoparticles containing PhS1P showed −12.42±0.22 mV, from which it was confirmed that the absolute value thereof was increased.

TABLE 2

| Nanoparticles | Concentration (%) | | | |
|---|---|---|---|---|
| | 0.5 | 1.0 | 1.5 | 2.0 |
| Typical lecithin nanoparticles | −1.43 ± 0.31 | −1.28 ± 0.402 | −0.85 ± 0.72 | −1.77 ± 0.31 |
| PhS1P-bile acid-conjugated nanoparticles | −17.34 ± 2.31 | −13.64 ± 0.52 | −12.42 ± 0.22 | −11.53 ± 0.52 |

The shape of the micelle nanoparticles was observed using an SEM (JEM1010, JEOL, Japan). Therefore, as shown in FIG. 2, the micelle nanoparticles were determined to be spherical nanoparticles having an average particle size of 120.3 nm.

Figure 3:
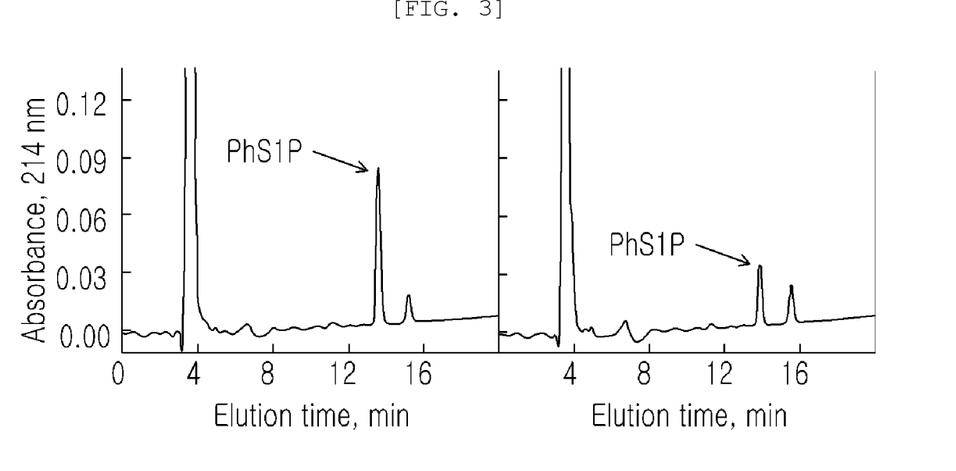
FIG. 3 shows the results of analysis of HPLC of the PhS1P-bile acid-conjugated micelle nanoparticles, (A): reference material, (B): PhS1P micelle nanoparticles.

In order to evaluate the presence or absence of PhS1P in the micelle nanoparticles through HPLC (Agilent 1200, Germany), conditions of absorbance at 214 nm and columns of ZORBAX Eclipse XDB-C18, 5 µm size, and 4.6 mm×150 mm were applied, and a mobile phase composed of methanol and purified water at 50 vol %:50 vol % was used. The flow rate was 0.8 ml/min, and the elution time at 30° C. was 10 to 16 min. A reference material was composed of methanol and purified water at 95 vol %:5 vol %, and the samples were also subjected to the same conditions and sonicated for 1 hr before use. Based on the results of HPLC in order to evaluate the presence of PhS1P in the micelle nanoparticles thus manufactured, as shown in FIG. 3, it was confirmed that the same peak appeared in the reference material and the micelle nanoparticles. Therefore, it was found that PhS1P was present in the manufactured micelle nanoparticles (in FIG. 3, left: reference material; and right: PhS1P-bile acid-conjugated nanoparticles).

INDUSTRIAL APPLICABILITY

The present invention can be widely used in cosmetic compositions.

The invention claimed is:
1. A micelle nanoparticle comprising bile acid and phytosphingosine-1-phosphate.
2. The micelle nanoparticle of claim 1, wherein the bile acid and the phytosphingosine-1-phosphate are conjugated to each other.
3. A cosmetic composition containing the micelle nanoparticle of claim 1.

* * * * *